(12) United States Patent
Benton et al.

(10) Patent No.: US 7,670,989 B2
(45) Date of Patent: Mar. 2, 2010

(54) NEUTRALIZING SUPERABSORBENT POLYMER COMPOSITION

(75) Inventors: Michael Benton, Ft. Worth, TX (US); Katrell Deon Copeland, Irving, TX (US); Robert C. Pearce, III, Arlington, TX (US); Alisha D. Roach, Irving, TX (US); John R. Roheim, Flower Mound, TX (US)

(73) Assignee: NCH Corporation, Irving, TX (US)

( * ) Notice: Subject to any disclaimer, the term of this patent is extended or adjusted under 35 U.S.C. 154(b) by 985 days.

(21) Appl. No.: 11/377,969

(22) Filed: Mar. 17, 2006

(65) Prior Publication Data

US 2007/0219302 A1 Sep. 20, 2007

(51) Int. Cl.
*B01J 20/26* (2006.01)
*B01J 20/04* (2006.01)
*C08K 3/26* (2006.01)

(52) U.S. Cl. ............... 502/402; 252/190; 510/476; 524/424; 524/505

(58) Field of Classification Search ............... 252/190; 510/476; 502/402; 524/424, 505, 917
See application file for complete search history.

(56) References Cited

U.S. PATENT DOCUMENTS

| | | | | |
|---|---|---|---|---|
| 3,994,821 | A | 11/1976 | Seidenberger | 252/192 |
| 4,707,348 | A | 11/1987 | Schuiling | 423/554 |
| 4,865,761 | A | 9/1989 | Mandel et al. | 252/190 |
| 5,342,543 | A | 8/1994 | Morris et al. | 252/190 |
| 6,264,846 | B1 * | 7/2001 | Smith | 210/749 |
| 6,692,656 | B1 | 2/2004 | McGillivray et al. | 252/192 |
| 2003/0134552 | A1 * | 7/2003 | Mehawej et al. | 442/118 |

OTHER PUBLICATIONS

Hawley's Condensed Chemical Dictionary, 14th Ed., 2002, entry for "Indicator".*

* cited by examiner

*Primary Examiner*—Fred M Teskin
(74) *Attorney, Agent, or Firm*—Locke Lord Bissell & Liddell, LLP

(57) ABSTRACT

An absorbent and process for the neutralization and absorption of acidic and alkaline liquid spills comprising a mixture of superabsorbent polymer, a styrene-butadiene-styrene block copolymer, sodium bicarbonate, and optionally a chlorine neutralizer. The absorbent preferably also contains a chlorine neutralizer for the neutralization of any chlorine vapors and a pH indicator to indicate that the spill has been neutralized and is safe for handling and disposal.

26 Claims, No Drawings

NEUTRALIZING SUPERABSORBENT POLYMER COMPOSITION

BACKGROUND OF THE INVENTION

1. Field of the Invention

The present invention is directed to an absorbent composition and more particularly to an absorbent composition that can absorb and neutralize any type of liquid spill, as well as indicate whether the spill is acidic, basic or neutral by a change in color. The absorbent also treats vapors, particularly those spills that emit chlorine.

2. Description of Related Art

Most known spill absorbents can absorb many times its weight in water; however, contact with the product after absorption of acid or alkali spills are still hazardous and must be neutralized or disposed of according to pH. Prior techniques show that an acid/base color-indicating absorbent will give the user some indication of the possible hazards associated with the spill. In addition, absorbents that neutralize both acids and alkalis reduce the danger of making contact with the product after absorption and eliminate hazardous waste disposal.

One such product, "Ampho-Mag"™ is an amphoteric buffer comprised of sulfuric acid, magnesium oxide and/or magnesium hydroxide, and water, available from Premier Chemicals LLC located in King of Prussia Pa. This sorbent also claims to meet the need for a non-caking, neutralizing amphoteric buffer with good storage properties, as opposed to a magnesia/Epsom salt blend, such as the one sold under the tradename "pH 9" by Terra Environmental. However, the use of a buffer that contains metals can result in unanticipated reactions and many of these absorbents must be conditioned in order to provide complete neutralization. Therefore, there is still a need for an improved neutralizing absorbent.

SUMMARY OF THE INVENTION

The present invention involves an absorbent and a process of using the absorbent to absorb and neutralize various types of spills and vapors. The absorbent comprises a mixture of a superabsorbent polymer, a styrene-butadiene-styrene block copolymer, and sodium bicarbonate. The absorbent preferably also contains a chlorine neutralizer for the neutralization of any chlorine vapors and a pH indicator to indicate that the spill has been neutralized and is safe for handling and disposal. Preferably the absorbent further resists hardening and caking during storage.

The absorbent can be said to be an efficient and effective neutralizer of both weak and strong acids and alkalis, as well as chlorine vapor. Therefore, it acts as an amphoteric buffer where acid and alkali spills are safe to handle and dispose of in a regular manner. This allows a single absorbent composition to be used on a wide variety of liquid spills. Another advantage of the present invention is that the absorbent does not require the presence of any metals other than sodium compounds in the sorbent and preferably is essentially free of other metals. Preferably, the absorbent also contains a chlorine-neutralizing compound to allow the absorbent to neutralize chlorine vapors, such as those generated from liquid spills containing bleach. The method of using the absorbent involves applying a sufficient amount of the novel absorbent to a liquid spill to neutralize and absorb the spill. An optional pH indicator in the absorbent can be used to determine when the spill has been sufficiently neutralized.

DETAILED DESCRIPTION OF THE PREFERRED EMBODIMENT

A preferred embodiment of the current invention can be prepared by adding appropriate amounts of sodium bicarbonate, and a styrene-butadiene-styrene block copolymer to a sodium polyacrylate polymer. In a more preferred embodiment, an appropriate amount of a chlorine neutralizer compound is also added to the other components. One or more pH indicator solution(s) are then preferably sprayed on the absorbent while mixing. The preferred absorbent provides good absorbency, indicates pH, neutralizes acids and alkalis, and stores without caking. In addition, it is free of metals other than sodium, easily manufactured, and it does not need conditioning with water for optimum neutralization, as in the prior art. The direct addition of components in the preferred embodiment of the present invention avoids intermediate compounds and reactions where hydration of metal compounds is pertinent for optimum use, as described in related art.

The high absorption rate of the preferred mixture is due to the addition of a sodium polyacrylate polymer. Without being bound by theory, it is currently believed that when hydrated, the carboxyl groups of the polymer dissociate into negatively charged carboxylate ions ($COO^{-1}$), which repel one another along the polymer chain. This widening of the polymer coils allows water to move into the proximity of more carboxyl groups, while maintaining a gel-like consistency from hydrogen bonding between the water and the carboxylate ions between chains. Then the spill can easily be picked up with a broom or squeegee and dustpan. The styrene-butadiene-styrene block copolymer is included in the absorbent composition to increase absorbency when working with oil-based spills.

The neutralizing property for both acids and alkalis makes this mixture amphoteric. The spill waste becomes safe to handle because the absorbent brings the pH to a range of 6-8. Sodium bicarbonate is capable of neutralizing acids by producing a sodium salt, water, and carbon dioxide. Reaction (1) is a representative reaction, which may occur when cleaning up a spill of phosphoric acid.

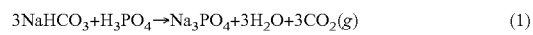

$$3NaHCO_3 + H_3PO_4 \rightarrow Na_3PO_4 + 3H_2O + 3CO_2(g) \quad (1)$$

The preferred superabsorbent polymer is also capable of neutralizing alkaline solutions as well. Acrylic acid is the monomer from which the preferred polymer is formed. Reaction (2) is representative of a reaction that may occur during clean up of a caustic spill. The polymers reliance on osmotic balance also aids in bringing the spill to a more neutral pH.

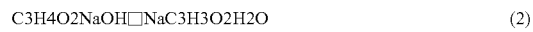

$$C_3H_4O_2NaOH \square NaC_3H_3O_2H_2O \quad (2)$$

This buffering effect produces a neutralized material with a pH very close to 7, which is significantly less dangerous than that of the un-neutralized acid or base.

Exposure to chlorine vapors is a big concern, especially with bleach spills. For this reason, a more preferred embodiment of the current invention also comprises a chlorine-neutralizing compound. Some neutralizers of this type include sodium sulfite, sodium thiosulfate, and ascorbic acid (or Vitamin C). Reaction (3) represents the reaction that may occur when applying the buffer to a bleach spill.

$$Na_2SO_3 + HOCl \rightarrow Na_2SO_4 + HCl \quad (3)$$

The addition of a chlorine neutralizer ensures a safer spill pick-up and avoids exposing the user to trapped chlorine vapors that would otherwise be released when disturbing the treated spill during clean up.

The addition of at least one pH indicator into the absorbent provides a visual way to confirm whether the spill has been neutralized to a safe pH level. The indicator serves as a warning to the user that the spill may be corrosive, and it should not be touched if there is a color change. Spraying the indicator as a water-based solution on the preferred absorbent while mixing is the best way of obtaining a consistent mixture. Convenient pH indicators include bromophenol blue, methyl yellow, phenolphthalein, phenol red, and thymolphthalein. The invention is not limited to those described: therefore, any indicator or combination that visually shows pH changes may be used. The amount of pH indicator that should be used in the absorbent is determined by the color intensity that is desired.

An attractive feature of the preferred absorbent is that it is free of metals other than sodium and does not require precise hydration of the product, as in prior art. The preferred absorbent is also able to absorb over forty times its weight in water. Therefore, even in humid conditions the product remains free flowing. Furthermore, the preferred absorbent can be manufactured using all solid components, with exception of the indicator(s) solution, making it possible to control manufacture of the final material in an economical and efficient manner. Also, the combination of components in the preferred absorbent lessens heat formation during spill clean up of all solutions, even more so than "Ampho-Mag"™. The ease of manufacture of the preferred absorbent eliminates undesirable caking and/or hardening during storage or application, and does so without excessive heat generation or the concern of conditioning the absorbent for complete neutralization. Once the product maintains its original color after completely covering the spill, it is considered neutralized.

The preferred method of production of the most preferred embodiment is the combination of superabsorbent polymer, a styrene-butadiene-styrene block copolymer, sodium bicarbonate, and a chlorine-neutralizing compound in a suitable mixer such as a ribbon mixer. The material is preferably processed batch wise. A preferred embodiment of the present invention is formed from components comprising by weight percent: superabsorbent polymer 25-60%, most preferably about 45%; styrene-butadiene-styrene block copolymer 20-35%, most preferably about 30%; sodium bicarbonate 10-50%, most preferably about 15%; chlorine neutralizing compound 5-20%, most preferably about 10%. The process aims to produce a product where the weight ratio of the above components is approximately 4.5:3.0:1.5:1.0, respectively. All of the components can be added to the mixer simultaneously before mixing. Once mixing has commenced, the pH indicator(s) can be sprayed into the mixture through the use of a suitable pump-up sprayer, such as a Hudson sprayer with a medium spray setting. Sizing of the resultant particles of the product should not be necessary. The raw materials are large enough to avoid dusting, but small enough to permit rapid reaction with the spill.

Example 1

Content Analysis for Metals

A sample of a preferred embodiment of the present invention containing the most preferred weight ratio of superabsorbent polymer, a styrene-butadiene-styrene block copolymer, sodium bicarbonate, and a chlorine-neutralizing compound was analyzed using the EPA 6000/7000 Series Metals method. The results confirmed that the product is indeed free of metals, unlike "Ampho-Mag"™, which is magnesium-based.

Example 2

Analysis for Off-Gassing of Chlorine Gas

The waste of a bleach spill treated with the absorbent prepared in Example 1 was analyzed for emission of chlorine gas using chlorine test strips. The color of the strip remained unchanged, even after disturbing the treated spill, indicating that the chlorine had been neutralized. Similarly, the same test was performed with the "Ampho-Mag" ™ absorbent. The chlorine test strip did not change color initially, but after disturbing the treated spill to clean it up, the strip changed color slightly, indicating the presence of about 10 ppm chlorine.

Example 3

Product Storage Handling Testing

A sample of the absorbent prepared in Example 1 was checked for its ability to resist "caking" under hot storage conditions. Duplicate samples were heated in a sealed vial in a convection oven at 120 degrees F. The samples were probed on a regular basis to check for "cake" formation. Neither sample showed any signs of hardening after 30 days at 120 degrees F.

Example 4

Neutralization Testing

The following preparations were carried out by mixing all the ingredients simultaneously in a ribbon mixer. Table 1 describes the chemical composition of Absorbents #1-4.

TABLE 1

|  | Absorbent #1 | Absorbent #2 | Absorbent #3 | Absorbent #4 |
| --- | --- | --- | --- | --- |
| Superabsorbent Polymer | 25% wt | 45% wt | 35% wt | 50% wt |
| Block Copolymer | 20% wt | 30% wt | 25% wt | 25% wt |
| Sodium Bicarbonate | 50% wt | 15% wt | 25% wt | 20% wt |
| Chlorine Neutralizer | 5% wt | 10% wt | 15% wt | 5% wt |

The ability of Absorbents #1-4 as well as "Ampho-Mag"™ absorbent to neutralize both acids and alkalis was evaluated by reacting each with 75% phosphoric acid or 50% caustic until neutralization was complete. The final pH was checked by wetting a spot of the treated spill with deionized water enough to use a pH paper strip. All of the formulations were capable of neutralizing both spills when the formulations were applied in excess of the stoichiometric quantity required for neutralization. These findings were also confirmed by using EPA method 9045C on a number of products that can be found in a grocery store. Even spill products with an original pH less than 0 or greater than 12 had a pH of 6-8 after treatment with the absorbents.

Example 5

Heat Generation of Superabsorbent Polymer-Based Absorbents #1-4

The reactions of Absorbents #1-4 generated considerably less heat than "Ampho-Mag"™ absorbent, as shown in Table 2. This analysis was performed with a Raytek infrared non-contact thermometer in conjunction with the procedure described in Example 4. The heat that was generated dissipated in a matter of minutes for Buffers #1-4, where as the heat generated by "Ampho-Mag"™ absorbent took considerably longer to reach room temperature.

TABLE 2

|  | Absorbent #1 | Absorbent #2 | Absorbent #3 | Absorbent #4 | "Ampho-Mag" ™ |
|---|---|---|---|---|---|
| Temperature w/ $H_2O$ (degrees F.) | Room Temperature | 77 | 75 | 78 | 95 |
| Temperature w/ 75% $H_3PO_4$ (degrees F.) | Room Temperature | Room Temperature | Room Temperature | Room Temperature | 130 |
| Temperature w/ 50% NaOH (degrees F.) | 100 | 90 | 96 | 92 | 141 |
| Temperature w/ bleach (degrees F.) | 93 | 101 | 107 | 93 | 91 |

Note:
Room temperature is 72 degree F.

The above descriptions of certain embodiments are made for the purposes of illustration only and are not intended to be limiting in any manner. Other alterations and modifications of the preferred embodiment will become apparent to those of ordinary skill in the art upon reading this disclosure, and it is intended that the scope of the invention disclosed herein be limited only by the broadest interpretation of the appended claims to which the inventor is legally entitled.

What is claimed is:

1. A particulate absorbent for the neutralization and absorption of a spill of aqueous or oil-based liquid comprising:
   from about 25 to about 60 weight percent superabsorbent polymer;
   from about 20 to about 35 weight percent styrene-butadiene-styrene block co-polymer;
   from about 10 to about 50 weight percent sodium bicarbonate; and
   from about 5 to about 20 weight percent chlorine neutralizing compound.

2. The absorbent of claim 1 further comprising a pH indicator.

3. The absorbent of claim 1 wherein the weight ratio of the superabsorbent polymer to styrene-butadiene-styrene block copolymer to sodium bicarbonate to chlorine neutralizing compound is about 4.5 to 3.0 to 1.5 to 1.0, respectively.

4. The absorbent of claim 1 wherein the absorbent is essentially free of metals other than sodium.

5. The absorbent of claim 1 wherein the superabsorbent polymer is a binding polyacrylate polymer.

6. The absorbent of claim 5 wherein the superabsorbent polymer is sodium polyacrylate polymer.

7. The absorbent of claim 1 wherein the absorbent is cake resistant.

8. The absorbent of claim 1 wherein the absorbent is capable of neutralizing both acidic and alkaline spills.

9. The absorbent of claim 1 wherein the chlorine neutralizing compound is selected from the group consisting of sodium thiosulfate, sodium sulfite, ascorbic acid, and mixtures thereof.

10. The absorbent of claim 1 comprising about 30 weight percent styrene-butadiene-styrene block copolymer.

11. The absorbent of claim 1 wherein the chlorine neutralizing compound is present in an amount of about 10 weight percent.

12. The absorbent of claim 3 further comprising a pH indicator.

13. The absorbent of claim 2 wherein the pH indicator is selected from the group consisting of bromophenol blue, methyl yellow, phenolphthalein, phenol red, thymolphthalein, and mixtures thereof.

14. A process for neutralizing and absorbing a spill of an acidic or alkaline, aqueous or oil-based liquid spill, the process comprising:
   identifying a liquid spill;
   applying to the spill in a quantity sufficient to neutralize and absorb the liquid a particulate absorbent comprising from about 25 to about 60 weight percent superabsorbent polymer; from about 20 to about 35 weight percent styrene-butadiene-styrene block co-polymer; from about 10 to about 50 weight percent sodium bicarbonate; and from about 5 to about 20 weight percent chlorine neutralizing compound.

15. The process of claim 14 wherein the absorbent further comprises a pH indicator.

16. The process of claim 14 wherein the superabsorbent polymer is present in the absorbent in an amount of about 45 wt. % and the bicarbonate is present in an amount of about 15 wt. %.

17. The process of claim 14 wherein the absorbent is essentially free of metals other than sodium.

18. The process of claim 14 wherein the superabsorbent polymer is a binding polyacrylate.

19. The process of claim 18 wherein the superabsorbent polymer is sodium polyacrylate polymer.

20. The process of claim 14 wherein the absorbent is cake resistant.

21. The process of claim 14 wherein the absorbent is not conditioned prior to being applied to the spill.

22. The process of claim 14 wherein the chlorine neutralizing compound is selected from the group consisting of sodium thiosulfate, sodium sulfite, ascorbic acid, and mixtures thereof.

23. The process of claim 14 wherein the weight ratio of the superabsorbent polymer to styrene-butadiene-styrene block copolymer to sodium bicarbonate to chlorine neutralizing compound is about 4.5 to 3.0 to 1.5 to 1.0, respectively.

24. The process of claim 14 wherein the chlorine neutralizing compound is present in the absorbent in an amount of about 10 weight percent.

25. The process of claim 14 wherein the neutralizing absorbent comprises about 30 weight percent styrene polybutadiene styrene styrene-butadiene-styrene block copolymer.

26. The process of claim 14 wherein the pH indicator is selected from the group consisting of bromophenol blue, methyl yellow, phenolphthalein, phenol red, thymolphthalein, and mixtures thereof.

* * * * *

UNITED STATES PATENT AND TRADEMARK OFFICE
CERTIFICATE OF CORRECTION

PATENT NO. : 7,670,989 B2  Page 1 of 1
APPLICATION NO. : 11/377969
DATED : March 2, 2010
INVENTOR(S) : Benton et al.

It is certified that error appears in the above-identified patent and that said Letters Patent is hereby corrected as shown below:

Col. 7, Lines 3-6
Claim 25 should read as follows:

"The process of claim 14 wherein the neutralizing absorbent comprises about 30 weight percent styrene-butadiene-styrene block copolymer."

Signed and Sealed this

Eleventh Day of May, 2010

David J. Kappos
*Director of the United States Patent and Trademark Office*